USOO5656588A

United States Patent [19]
Zaloga et al.

[11] Patent Number: 5,656,588
[45] Date of Patent: Aug. 12, 1997

[54] WOUND HEALING FORMULA

[75] Inventors: Gary P. Zaloga; Pamela Roberts, both of Winston-Salem, N.C.

[73] Assignee: Wake Forest University, Winston-Salem, N.C.

[21] Appl. No.: 276,955

[22] Filed: Jul. 19, 1994

[51] Int. Cl.$^6$ .......................... A61K 38/05; A61K 31/70
[52] U.S. Cl. ...................... 514/2; 514/19; 514/21; 514/23
[58] Field of Search ...................... 514/2, 19, 21, 514/23; 426/656, 657

[56] References Cited

U.S. PATENT DOCUMENTS

| | | | |
|---|---|---|---|
| 4,049,831 | 9/1977 | Ono et al. | 426/72 |
| 4,359,416 | 11/1982 | Vinick | 548/344 |
| 5,164,367 | 11/1992 | Pickart | 514/6 |
| 5,221,668 | 6/1993 | Henningfield et al. | 514/23 |

FOREIGN PATENT DOCUMENTS

| | | |
|---|---|---|
| 192317 | 2/1990 | European Pat. Off. |

OTHER PUBLICATIONS

Ther. Res., vol. 13, No. 4, Kuwayama Hajime et al., 1992, abstract.

Fitzpatrick et al, *Histamine synthesis, imidazole dipeptides, and wound healing*, Surgery, vol. 91, No. 4, pp. 430–434 (1982).

Fitzpatrick et al, *Carnosine, histidine, and wound healing*, Surgery, vol. 91, No. 1, pp. 56–60 (1982).

Kunimi et al, *Effects of CL–1700 on Duodenal Ulcer Formation in the Rat*, Japan. J. Pharmacol. No. 32, pp. 1167–1170 (1982).

Kunimi et al, *Effects of CL–1700 and Its Constituents on Acute or Chronic Gastric Lesions and Gastric Secretion in Rats*, Japan. J. Pharmacol. No. 32, pp. 469–477 (1982).

Nagai et al, *Action of carnosine and β–alanine on wound healing*, Surgery, vol. 100, No. 5, pp. 815–821 (1986).

Okabe et al, *Effects of N–AcetylL–Carnosine Aluminum (CL–1700) on Various Acute Gastric Lesions and Gastric Secretion in Rats*, Japan. J. Pharmacol. No. 31, pp. 941–950 (1981).

Vizioli et al, *Effect of Carnosine on the Development of Rat Sponge–Induced Granulation I. General Morphology and Glycosaminoglycans Histophotometry*, Cellular & Molecular Biology No. 23, pp. 267–273 (1978).

*Primary Examiner*—José G. Dees
*Assistant Examiner*—Rosalynd Williams
*Attorney, Agent, or Firm*—Dann, Dorfman, Herrell And Skillman

[57] ABSTRACT

The present invention provides a composition that stimulates and improves wound healing in a patient in need of same. To this end, a method for stimulating wound healing comprising the step of administering to a patient a composition including a therapeutically effective amount of a source of carnosine is provided. In an embodiment, the composition also meets the nutrient requirements of a patient that are generated due to tissue repair and healing requirements.

13 Claims, No Drawings

WOUND HEALING FORMULA

BACKGROUND OF THE INVENTION

The present invention generally relates to nutritional compositions. More specifically, the present invention relates to compositions for use in stimulating and improving wound healing.

Integuments surrounding tissues or organs of the body serve vital functions. One of the primary functions is to protect the soft internal tissues from physical trauma and bacteriological invasion. As a result, when an integument is lacerated or broken due to, for example, surgery or trauma, damage to the underlying tissues usually occurs.

For example, by virtue of its location at the body surface, the skin is constantly exposed to physical insult. Such insults range from minor abrasions to deep wounds that may penetrate to the subcutaneous tissues. The way in which the skin responds to this range of potential trauma varies depending on the severity of the trauma. In any case, however, a delay in the wound healing process increases the susceptibility to infection. Therefore, the acceleration of the healing process remains an elusive goal of the scientific community.

The pathophysiology of wound healing is complex and multifactorial. Current concepts suggest that healing involves the following mechanisms: (1) inflammation; (2) fibroblast proliferation, collagen synthesis; (3) angiogenesis; (4) wound contracture; and (5) epithelialization. See, for example, Roberts, *Nutrition and Wound Healing*, Nutrition in Critical Care, (Zaloga G. P. ed.) Mosby, St. Louis, pp. 525–544 (1994); and Cohen et al, *Wound Healing-Biochemical and Clinical Aspects*, (Lindblad W. J. eds.), W. B. Saunders, Philadelphia, pp. 1–630 (1992). Numerous factors, including metabolic factors, immune function, cytokines, eicosanoids, free radical production, and nutrient availability, affect these mechanisms.

Optimal wound healing requires delivery of a variety of nutrients to the wound. For example, nitrogen, vitamins (i.e. vitamin C) and minerals (i.e. zinc, magnesium, phosphorus, potassium) are required for wounds to heal. Id. Likewise, protein depletion impairs wound healing and, therefore, adequate protein intake is recognized to be essential for optimal wound healing. Still further, some studies suggest that supplementation of the diet with arginine improves wound healing in animals and humans. See, for example, Barbul et al, *Intravenous Hyperalimentation with High Arginine Levels Improves Wound Healing and Immune Function*, J. Surg. Res., 38:328–334 (1985); and Kirk et al, *Arginine Stimulates Wound Healing and Immune Function in Elderly Human Beings*, Surgery, 114:155–160 (1993).

In addition to the above nutrients, some researchers have postulated that carnosine may have an effect on wound healing when administered as a peptide via intradermal (ie. into the wound) or intraperitoneal injection. See, for example, Fitzpatrick et al, *Carnosine, histidine and wound healing*, Surgery, 91: 56–60 (1982); and Nagai et al, *Action of carnosine and β-alanine on wound healing*, Surgery, 100: 815–820 (1986). Naturally, administering the peptide via intradermal and intraperitoneal injection is intrusive, and time-consuming.

In yet other studies dealing with ulcer prevention as opposed to healing, investigators have reported that N-acetyl-L-carnosine aluminum protects against the formation of gastric and duodenal ulcers in food deprived rats. See, for example, Okabe et al, *Effects of N-Acetyl-L-Carnosine Aluminum (CL-1700) on Various Acute Gastric Lesions and Gastric Secretion in Rats*, Japan J. Pharmacol, 31: 941–950 (1981); and Kunimi et al, *Effects of CL-1700 on Duodenal Ulcer Formation in the Rat*, Japan J. Pharmacol, 32: 1167–1170 (1982). As noted in these studies, some of the protective effect of this compound appears to result from the aluminum salt. The studies suggest that N-acetyl-L-carnosine aluminum and carnosine have different effects on ulcer formation.

Providing a suitable enteral diet or supplement that likewise stimulates wound healing would be advantageous. These diets can either be administered through a nasogastric tube or other external means or provided in liquid form that the patient drinks. Moreover, in many situations, it would be beneficial to support a trauma patient with a complete nutritional formula, while at the same time stimulate wound healing.

Numerous enteral formulations have been targeted for trauma and burn patients. These products include: Mead-Johnson's TraumaCal®; Sandoz's Impact®; Abbott Laboratories' Alitraq® and Perative®; and McGaw's Immun-Aid®.

Although these products are used in an attempt to treat and/or provide nutritional requirements to such patients, the inventors of the present invention do not believe these products meet all the requirements of such patients. Delayed wound healing in such patients predisposes patients to infection, prolonged hospital stay, prolonged recovery and rehabilitation, increased hospitalization costs, and increased mortality.

Accordingly, a need exists for a new mode of therapy for improving wound healing in such patients.

SUMMARY OF THE INVENTION

The present invention provides a composition for stimulating wound healing. The present invention also meets the unique nutrient needs of the patients that are generated due to tissue repair and healing requirements.

Pursuant to the present invention, a composition comprising a protein source including a therapeutically effective amount of a source of carnosine, a carbohydrate source, and a lipid source is provided. The source of carnosine effectively acts to stimulate wound healing.

In an embodiment, the carnosine provides at least 2% of the total calories of the composition.

In an embodiment, the composition includes a source of arginine.

In an embodiment, the composition includes vitamins, minerals and trace elements.

The present invention also provides an improved method for stimulating and improving wound healing. In an embodiment, the method includes enterally administering to a patient a composition including a therapeutically effective amount of a source of carnosine. The carnosine may be given as a supplement or part of a complete nutritional formula.

In another embodiment, the present invention provides a method for stimulating and improving wound healing comprising administering to a patient a therapeutically effective amount of a composition comprised of: a protein source including a source of carnosine; a carbohydrate source; and a lipid source.

In an embodiment, the present invention provides a method for treating a patient having increased wound healing requirements comprising administering to the patient a therapeutically effective amount of a composition comprised of: a protein source including a source of carnosine; a carbohydrate source; and a lipid source.

An advantage of the present invention is that it provides a composition that is designed to stimulate wound healing in patients.

Moreover, an advantage of the present invention is that it not only provides a supplement that effectively improves wound healing, but also provides a total composition that contains all necessary nutrients.

Still further, an advantage of the present invention is that it is a ready-to-use composition, and not a powder that requires reconstitution before use, reducing the risk of bacterial contamination during the mixing process.

Moreover, an advantage of the present invention is that it utilizes a specific dipeptide, namely carnosine, that promotes healing and tissue repair-cell division.

Additionally, an advantage of the present invention is that it provides a composition that improves the healing rates of wounds.

Yet another advantage of the present invention is that it can be used for the treatment of wounds in patients with impaired wound healing due to chemotherapy agents.

Additional features and advantages of the present invention are described in, and will be apparent from, the detailed description of the presently preferred embodiments.

DETAILED DESCRIPTION OF THE PRESENTLY PREFERRED EMBODIMENTS

The present invention provides compositions specifically designed for use with patients suffering from a variety of wounds or having increased wound healing requirements. For example, patients suffering from surgical wounds, traumatic wounds, fractures, burn injuries, and decubiti ulcers, among others, may be treated pursuant to the present invention. The compositions of the present invention stimulate and improve wound healing, reducing the chances of infection due to delayed wound healing.

Pursuant to the present invention, a ready-to-use composition is provided. The composition includes a therapeutically effective amount of a source of carnosine. Suitable sources of carnosine are carnosine in peptide form (β-alanyl-histidine) or muscle protein, which is an endogenous source of carnosine.

In an embodiment, the source of carnosine comprises approximately 2% to about 10% of the total calories of the composition. In a preferred embodiment, the source of carnosine provides at least 2% of the total calories of the composition. The source of carnosine may be given as a supplement or as part of a complete diet. When the carnosine is part of a, complete formula, the formula preferably includes a protein source, a lipid source, and a carbohydrate source.

The composition preferably includes a high protein content to adequately support wound healing. In an embodiment, the protein source comprises approximately 20% to 35% of the total calories of the composition.

A variety of proteins can be utilized pursuant to the present invention. Suitable protein sources are milk (casein, whey), vegetable (soy), or meat proteins. The protein source can be either intact protein, hydrolyzed protein (ie. peptides produced by protein degradation), and/or an amino acid-containing diet. To further improve wound healing, the protein source can also include a source of arginine. In an embodiment, the composition includes from approximately 2% to 10% of the total calories as arginine.

In a preferred embodiment, the protein source comprises 50% to 100% hydrolyzed protein. The inventors have discovered that peptide based diets promote improved growth rates and healing in animals as compared to amino acid and intact protein diets. Table 1 below illustrates these improved healing rates.

TABLE 1

| Diet | Wound Strength (abdominal bursting pressure) |
| --- | --- |
| Peptide diet | 172 ± 34 mm Hg |
| Intact protein diet | 159 ± 29 mm Hg |
| Amino acid diet | 135 ± 42 mm Hg |

The composition of the present invention also includes a lipid source. Preferably, approximately 20% to about 40% of the composition, by calories, is provided as a lipid. Suitable lipids that may be utilized pursuant to the present invention are medium chain triglyceride oil, sunflower oil, soy oil, or fish oil.

The composition also includes a carbohydrate source. The carbohydrate source comprises approximately 30% to about 50% of the total calories of the composition. By way of example, the carbohydrates can be chosen from maltodextrin, corn starch, sucrose, and corn syrup solids.

Still further, the composition may include the recommended dietary intakes of minerals, vitamins, and trace elements. However, preferably, the composition includes higher than the recommended dietary intake of vitamins C, E, A, and zinc. In an embodiment, the composition includes: approximately 700 mg/day to about 3000 mg/day of Vitamin C; approximately 40 IU/day to about 400 IU/day of Vitamin E; approximately 15,000 IU/day to about 30,000 IU/day of Vitamin A; and approximately 30 mg/day to about 90 mg/day of zinc.

By way of example, and not limitation, an example of a composition of the present invention will now be given.

EXAMPLE #1

| | |
| --- | --- |
| Protein | 20–35% of calories |
| Intact protein or Peptides | 50 g/l |
| Arginine | 20–30 g/l |
| Carnosine | 10–30 g/l |
| Vitamin C | 0.7–1.4 g/l |
| Vitamin E | 20–40 IU/l |
| Vitamin A | 10,000–18,000 IU/l |
| Zinc | 20–30 mg/l |
| Lipid | 20–40% of calories |
| MCT Oil, Sunflower or Soy Oil | |
| Carbohydrate | 30–50% of calories |
| Maltodextrin, Starch | |

The present invention further provides methods for improving wound healing in a patient in need of same. The compositions of the present invention may be administered orally, enterally, parenterally (ie. intravenous, subcutaneous), or transdermally.

With respect to the treatment aspect, the composition may be utilized to treat a variety of wound conditions. For example, the present invention may be utilized in the treatment of patients with surgical wounds, traumatic wounds, fractures, burn injuries, and decubiti ulcers, among others. Still further, the present invention may be utilized in the treatment of wounds in patients with impaired wound healing resulting from the use of glucocorticoids and antimetabolites (ie. chemotherapy agents).

Pursuant to the present invention, therapeutically effective amounts of carnosine are supplemented with a complete diet. Upon administering the composition to the patient, the inventors have discovered that supplemental carnosine improves wound healing in mammals that are not nutritionally deprived.

Notably, the inventors have discovered that supplemental histidine and β-alanine did not improve wound healing in such patients. Previous studies in this area have advocated that the wound healing effects can be achieved with histamine or histidine. As the results indicate in Table 2, carnosine proved more effective in stimulating wound healing than histidine treatment. Table 2 illustrates comparative results between carnosine and histidine administered to animals following surgery.

TABLE 2

| Diet | Wound Strength (abdominal burstinq strength) |
| --- | --- |
| Diet + carnosine | 143 ± 10 mm Hg |
| Diet + β-alanine & histidine | 115 ± 8 mm Hg |

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

We claim:

1. A method for stimulating and improving wound healing in a patient in need of same comprising enterally administering to said patient a composition including a source of uncomplexed carnosine in an amount effective to stimulate wound healing.

2. The method of claim 1 wherein the carnosine provides at least 2% of the total calories of the composition.

3. The method of claim 1 wherein the composition further comprises: a protein source; a carbohydrate source; and a lipid source.

4. The method of claim 3 wherein the protein source includes a majority of the protein calories as partially hydrolyzed proteins.

5. The method of claim 1 wherein the composition includes a source of arginine.

6. The method of claim 1 further comprising feeding the composition through a tube to the patient.

7. A method for stimulating and improving wound healing in a patient in need of same comprising externally administering to the patient a therapeutically effective amount of a composition comprising:

a protein source including a source of uncomplexed carnosine in an amount effective to stimulate wound healing;

a carbohydrate source; and a lipid source.

8. The method of claim 7 wherein the carnosine provides at least 2% of the total calories of the composition.

9. The method of claim 7 wherein the composition is administered enterally.

10. The method of claim 7 wherein the protein source comprises approximately 20% to about 35% of the total calories of the composition.

11. The method of claim 7 wherein the lipid source comprises approximately 30% to about 40% of the total calories of the composition.

12. The method of claim 7 wherein the carbohydrate source comprises approximately 30% to about 40% of the total calories of the composition.

13. A method for treating a patient having increased wound healing requirements comprising externally administering to the patient a therapeutically effective amount of a composition comprising:

a protein source including a source of uncomplexed carnosine in an amount effective to stimulate wound healing;

a carbohydrate source; and a lipid source.

* * * * *